United States Patent [19]
Okihara

[11] Patent Number: 5,892,225
[45] Date of Patent: Apr. 6, 1999

[54] METHOD OF PREPARING A PLAN-VIEW SAMPLE OF AN INTEGRATED CIRCUIT FOR TRANSMISSION ELECTRON MICROSCOPY, AND METHODS OF OBSERVING THE SAMPLE

[75] Inventor: Masao Okihara, Tokyo, Japan

[73] Assignee: Oki Electric Industry Co., Ltd., Tokyo, Japan

[21] Appl. No.: 766,613

[22] Filed: Dec. 13, 1996

[30]     Foreign Application Priority Data

Jan. 9, 1996  [JP]  Japan ................................ 8-001768

[51] Int. Cl.⁶ ........................... H01J 37/295; H01J 37/26
[52] U.S. Cl. ............................ 250/311; 250/307
[58] Field of Search .................... 250/307, 306, 250/311, 440.11

[56]           References Cited

U.S. PATENT DOCUMENTS

| | | | |
|---|---|---|---|
| 4,508,952 | 4/1985 | Mochel et al. | 219/121 |
| 4,866,273 | 9/1989 | Kobayashi et al. | 250/311 |
| 4,888,304 | 12/1989 | Nakagawa et al. | 437/86 |
| 5,278,408 | 1/1994 | Kakibayashi et al. | 250/311 |
| 5,475,218 | 12/1995 | Kakibayashi et al. | 250/311 |
| 5,640,539 | 6/1997 | Goishi et al. | 250/310 |

FOREIGN PATENT DOCUMENTS 0 513 776 A  11/1992  European Pat. Off. .
41 12 375 A1  10/1992  Germany .

OTHER PUBLICATIONS

Patent Abstracts of Japan, vol. 95, No. 1, 7 Oct. 1994 & JP 06 281551 A (Sharp Corporation).

Taritomo et al., "Application of the Focused–Ion–Beam Technique for Preparing the Cross–Section Sample of Chemical Vapor Deposition Diamond Thin Film for High–Resolution Transmission Electron Microscope Observation", *Japanse Journal of Applied Physics*, vol. 31 (1992), pp. L1305–L1308.

*Primary Examiner*—Bruce Anderson
*Attorney, Agent, or Firm*—Jones & Volentine, L.L.P.

[57]               ABSTRACT

A plan-view sample of an integrated circuit is prepared for transmission electron microscopy by marking a faulty circuit element, lapping the upper surface of the sample to a mirror finish, lapping the lower surface to reduce the thickness of the entire sample, and further processing the lower surface by lapping or dimpling, combined with ion milling as necessary, to thin the sample in the vicinity of the fault. A sample prepared in this way affords a wide view, and can be tilted at large angles. A known thickness of a particular type of layer in the sample can be left by holding the sample at a predetermined angle while the sample is lapped.

20 Claims, 12 Drawing Sheets

METHOD OF PREPARING A PLAN-VIEW SAMPLE OF AN INTEGRATED CIRCUIT FOR TRANSMISSION ELECTRON MICROSCOPY, AND METHODS OF OBSERVING THE SAMPLE

BACKGROUND OF THE INVENTION

The present invention relates to methods of preparing samples of semiconductor integrated circuits for observation with a transmission electron microscope, and methods of analyzing defects by means of such samples.

The transmission electron microscope (hereinafter, TEM) is often used to observe and analyze the causes of faults that occur in integrated circuits, particular in very-large-scale or ultra-large-scale integrated circuits (VLSI or ULSI circuits). Since a VLSI or ULSI circuit may contain several million transistors and other circuit elements, the first step is to isolate the fault to a particular circuit element and mark the fault site. The integrated circuit is normally too large to be placed in the TEM sample holder, so a sample containing the marked site is taken from the integrated circuit. The sample is further prepared for TEM observation by thinning a small region around the marked site to permit penetration by the electron beam in the TEM. Known sample preparation techniques include optical beam induced current (OBIC) analysis to locate the fault, and lapping, dimpling, ion milling, and focused-ion-beam (FIB) processing to reduce the region around the fault site to a thin slice.

A problem with many conventional sample-preparation methods is that, although the region around the marked site is thinned, most of the rest of the sample is left unthinned. When placed in the TEM, the sample can only be tilted at certain restricted angles without having the remaining thick portions of the sample obstruct the electron beam. This restriction on the tilt angle prevents certain desirable types of observation and analysis from being carried out.

A second problem is that the small thinned section may not provide adequate visualization of the structural defect that caused the fault. This is particularly true in samples prepared for cross-sectional observation, since the thin section often does not reveal the full extent of the defect, and sometimes misses the defect entirely.

With plan-view sample geometries, a third problem arises from the layered structure of the sample. With conventional preparation techniques, it is difficult to determine the individual thicknesses of the layers encountered by the electron beam, hence difficult to perform an accurate analysis of the information provided by the TEM observations. In particular, accurate elemental analysis becomes difficult.

SUMMARY OF THE INVENTION

It is accordingly an object of the present invention to obtain adequate visualization of structural defects by TEM observation of a sample of an integrated circuit.

Another object of the invention is to enable the sample to be tilted for TEM observation from a wide range of angles.

Yet another object is to perform accurate elemental analysis.

The invented sample preparation method begins by marking a faulty circuit element in an integrated circuit, and excising a sample containing the faulty circuit element. The excised sample, like the integrated circuit itself, comprises a substrate covered by one or more upper layers.

Next, both the upper and lower surfaces of the sample are lapped, reducing the sample thickness to about one tenth of a millimeter. The upper surface of the sample is given a mirror finish, thereby removing upper layers that would interfere with TEM observation.

The lower surface of said sample is then further thinned in the region below the faulty circuit element, to a thickness permitting the TEM's electron beam to penetrate through the sample. Dimpling or lapping can be used as the further thinning method, in combination with ion milling as necessary.

The invented sample preparation method permits either a known thickness of upper layers of the integrated circuit to be left above the substrate at the fault site, or a known thickness of substrate to be left below the fault site. The known thickness can be established by holding the sample at a predetermined angle when the upper surface or lower surface is lapped.

When a sample prepared in this way is observed in a TEM, a plan view of a relatively large area can be obtained. The sample can be tilted at substantially unrestricted angles, including large angles, permitting various analytical techniques to be employed. Moreover, effects due to the known thickness of the substrate or upper layers can be subtracted from the TEM measurements, enabling elemental analysis, for example, to be carried out accurately.

DETAILED DESCRIPTION OF THE INVENTION

Figure 1:
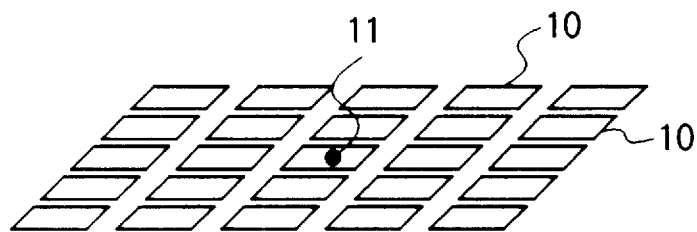
FIG. 1 is a perspective view of part of an integrated circuit, illustrating the location of a fault.

The invention will be described by way of example with reference to the embodiments illustrated in the drawings.

First, a general method of preparing a plan-view sample of an integrated circuit without leaving any thick sample portions will be described.

FIG. 1 represents part of the surface of, for example, a faulty VLSI device. The device has a large number of circuit elements 10 such as transistors formed in a semiconductor substrate. The substrate is covered by layers of various insulating and conducting materials, not explicitly shown in this drawing.

The first step in sample preparation is to isolate the fault site 11 to a particular circuit element. This step can be carried out by conventional methods of fault analysis such as OBIC analysis. These methods can also determine whether the fault is located in the substrate or in an upper layer.

Figure 2:
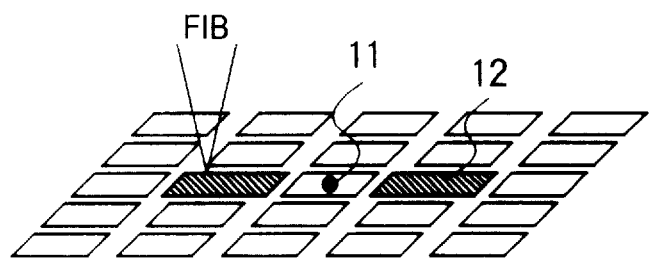
FIG. 2 illustrates the marking of the fault in FIG. 1.
Figure 3:
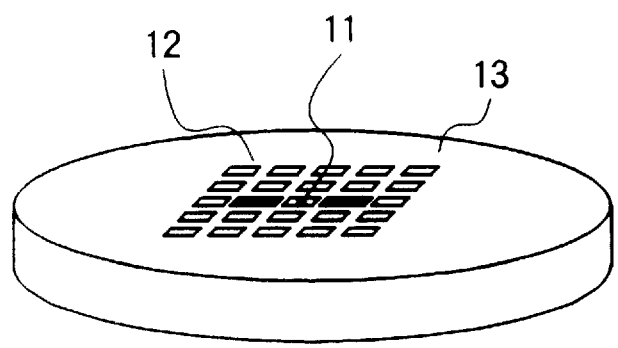
FIG. 3 illustrates the excision of a sample containing the fault.

Next, with reference to the OBIC data, for example, the fault site 11 is marked as shown in FIG. 2, by using a focused ion beam (FIB) to make markings 12 on two opposite sides of the faulty circuit element. The markings 12 can have any convenient shape, but should be observable with an optical microscope.

Next a dicing saw, for example, is used to excise a sample 13 from the device. The sample has the shape of a circular disk with a diameter small enough to fit the sample holder in the TEM, typically a diameter of about three millimeters (3 mm). The cutting is performed under optical microscope observation, and is controlled so that the markings 12 around the fault site 11 are positioned at substantially the center of the sample 13.

Figure 4:
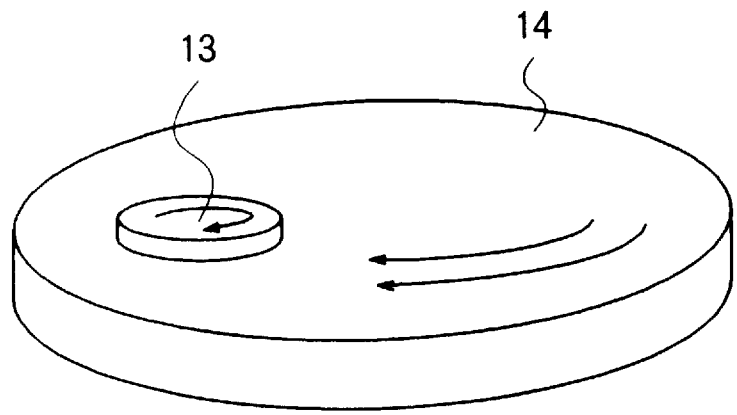
FIG. 4 illustrates the lapping of the upper surface of the sample.
Figure 5:
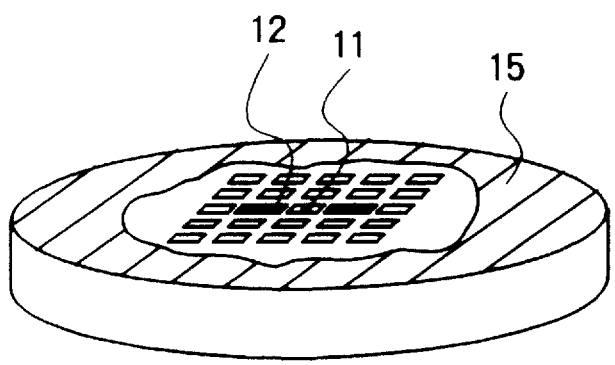
FIG. 5 illustrates the upper surface at an intermediate stage of lapping.

Next the upper surface of the sample 13 is lapped as shown in FIG. 4, by placing the sample 13 upside-down on a rotating lap 14. The sample 13 is held in such a way that the sample itself can rotate while being lapped, as indicated by the arrows. Lapping therefore proceeds from the periphery of the sample 13 in toward the center, as illustrated in FIG. 5. The sample-holding apparatus will be described later.

Figure 6:
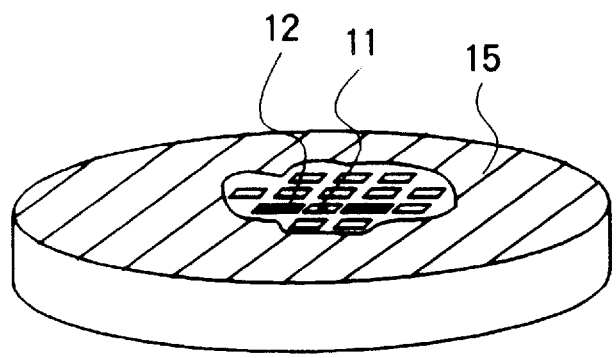
FIG. 6 illustrates the upper surface at a final stage of lapping.

The lapping process removes one or more of the upper layers of the sample 13 and polishes the exposed surface to a mirror finish. The progress of the lapping process can be followed by noting the advance of visible boundaries on the polished surface, such as the boundary between the exposed substrate area 15 and the area where the substrate remains covered by one or more upper layers. Lapping continues until sufficient material has been removed from the surface of the sample 13 to permit TEM observation of the fault site 11. The lapping process can be stopped when, for example, the boundary between the exposed substrate area 15 and upper layers approaches to a certain short distance from the fault site 11 between the markings 12, as shown in FIG. 6. Most of the thickness of the upper layers above the substrate will then have been removed at the fault site 11; in particular, the thick surface passivation layer with which a semiconductor integrated circuit is commonly covered will have been mostly or entirely removed.

Figure 7:
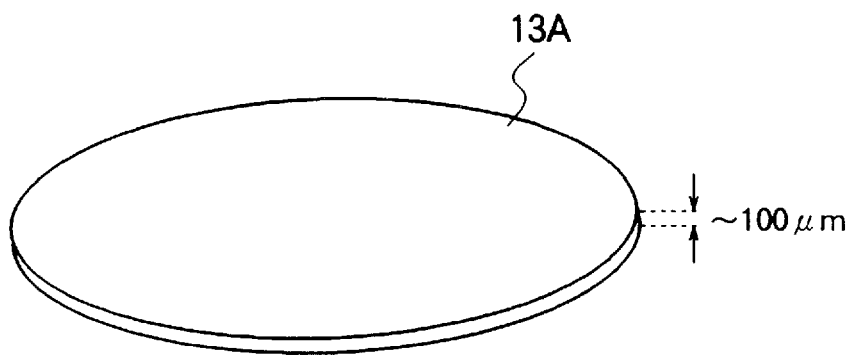
FIG. 7 illustrates the sample after lapping of the lower surface.

Next the undersurface 13A of the sample 13 is lapped. Lapping of the undersurface continues until the sample thickness has been reduced to substantially one hundred micrometers (100 $\mu$m), for example, as shown in FIG. 7.

Figure 8:
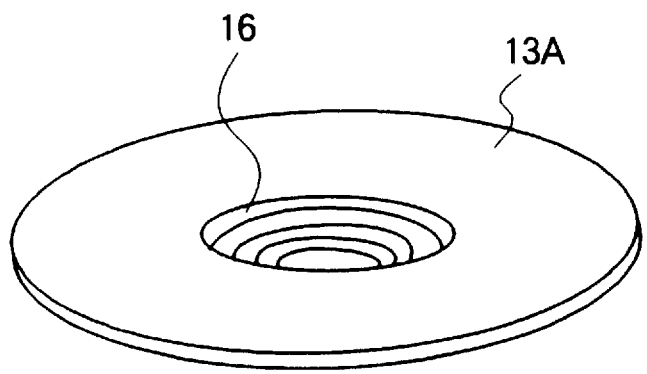
FIG. 8 illustrates the dimpling of the lower surface.

A dimple 16 is next created in the undersurface 13A of the sample, as shown in FIG. 8. The dimple is positioned in the center of the sample. The sample thickness at the deepest part of the dimple is thereby reduced to substantially ten micrometers (10 $\mu$m).

Figure 9:
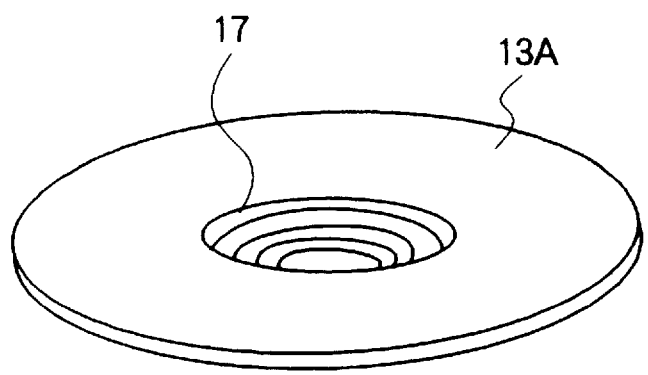
FIG. 9 illustrates ion milling of the dimple.

Finally, the sample thickness in the dimple is further reduced by ion milling. FIG. 9 illustrates the ion-milled surface 17. In this way the central part of the sample 13 is thinned sufficiently to permit the TEM's electron beam to penetrate through the sample at the fault site and in a comparatively large surrounding region.

Figure 10:
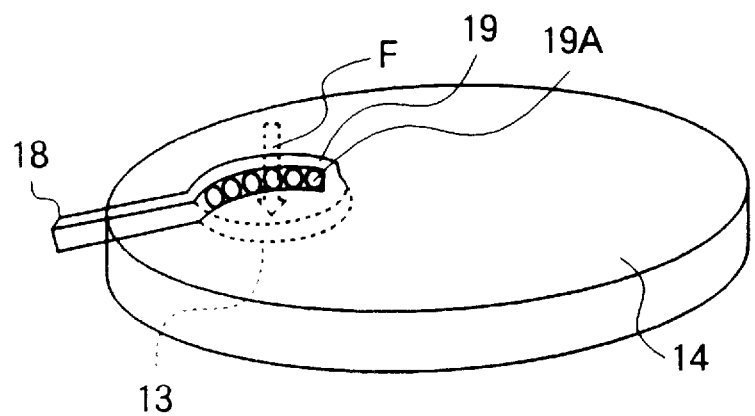
FIG. 10 shows how the sample is held while the upper surface is being lapped.

FIG. 10 shows the holding apparatus that permits the sample 13 to rotate while being lapped. This apparatus comprises an arm 18 having an arcuate tip 19 with spherical rollers 19A. The arcuate tip 19 is designed to fit against the edge of the sample 13; the rollers 19A permit the sample to turn. A weight (not visible) is placed on the sample 13 to exert a force F pressing the sample 13 against the lap 14.

Next, several variations of this basic sample preparation method will be described.

Figure 11:
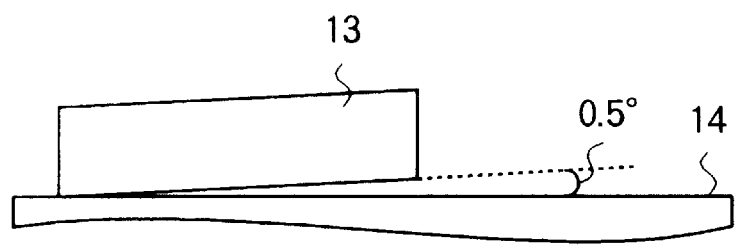
FIG. 11 illustrates another method of lapping the upper surface.
Figure 12:
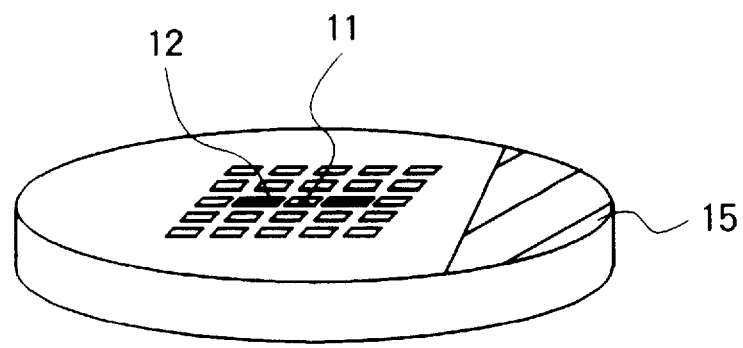
FIG. 12 illustrates the upper surface at an intermediate stage of lapping.
Figure 13:
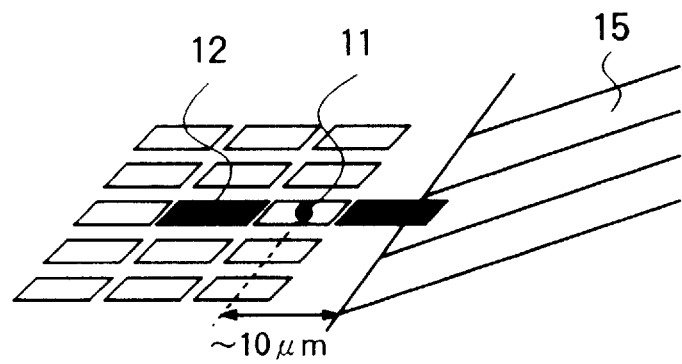
FIG. 13 illustrates the point at which lapping of the upper surface is stopped.

The first variation concerns the lapping of the upper surface of the sample. Instead of being held by the apparatus shown in FIG. 10, the sample 13 is held as shown in FIG. 11, tilted at a small fixed angle such as 0.5° to the surface of the lap 14. The sample 13 does not rotate, so lapping advances from one edge of the sample toward the opposite edge, as illustrated in FIG. 12. Lapping is stopped when the boundary of the exposed substrate area 15 is located a certain distance, such as ten micrometers (10 $\mu$m), from the fault site 11 between the markings 12, as illustrated in FIG. 13.

Figure 14:
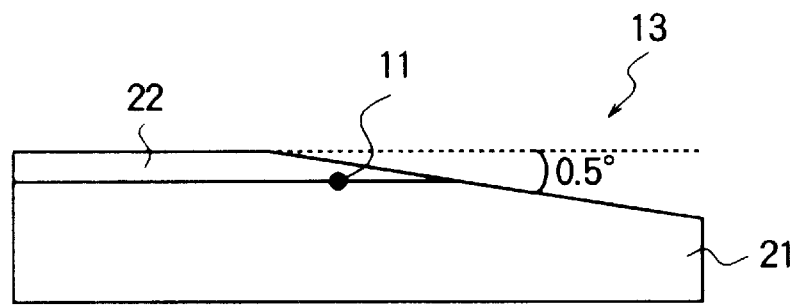
FIG. 14 is a sectional view of the sample after lapping as in FIGS. 11 to 13.
Figure 15:
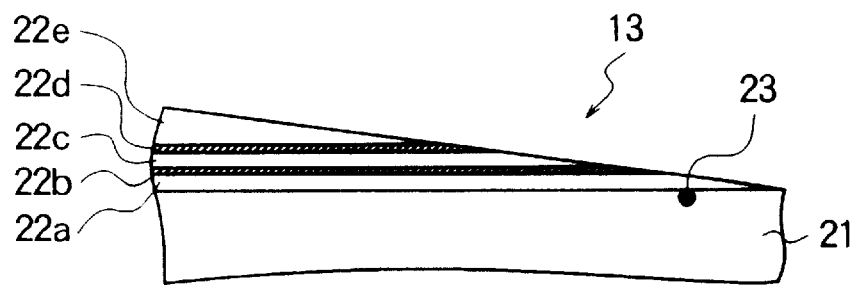
FIG. 15 shows an enlarged view of part of FIG. 14.

At this point the sample 13 has the cross-sectional appearance shown in FIG. 14, comprising a substrate 21 and upper layers 22. The substrate 21 comprises, for example, crystalline silicon. The upper layers 22 comprise, for example, a first insulating layer 22a, a first metal interconnection layer 22b, a second insulating layer 22c, a second metal interconnection layer 22d, and a passivation layer 22e, as shown in FIG. 15. If the defect 23 that caused the fault is located in the substrate 21 below the first insulating layer 22a, a simple trigonometric calculation shows that the thickness of the upper layers 22 remaining above the defect 23 is only 0.1 $\mu$m.

If necessary, the thickness of the upper layers 22 remaining above the defect 23 can be further reduced, by reducing the above-mentioned angle from 0.5° to a smaller angle, or by allowing the edge of the exposed substrate area 15 to approach the fault site 11 more closely.

The underside of the sample 13 is then processed by lapping, dimpling, and ion milling as shown in FIGS. 7 to 9. In this way a sample with a precisely known upper-layer thickness at the fault site 11 can be prepared.

Figure 16:
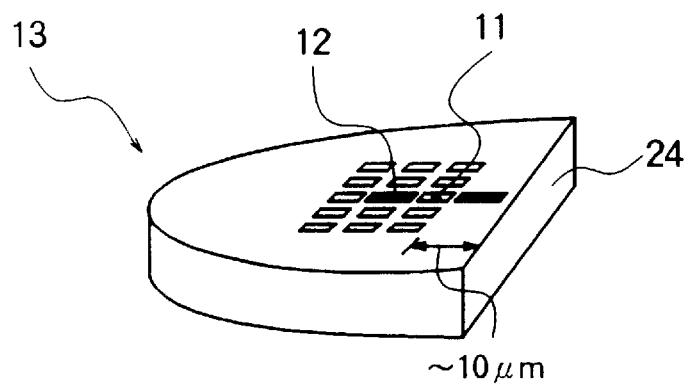
FIG. 16 illustrates a cut that can be made in the sample after the upper surface has been lapped.

The second variation provides a way to position the dimple 16 accurately. Referring to FIG. 16, after the upper surface of the sample 13 has been lapped as in FIGS. 4 to 6, or as in the first variation in FIGS. 11 to 15, the sample is cut with a dicing saw or other means along a line disposed ten micrometers (10 μm), for example, from the fault site 11 between the markings 12. If the upper surface was lapped as in FIGS. 11 to 15, the cut edge 24 should be parallel to the edge of the exposed substrate area 15 shown in FIG. 13, or should coincide with this edge.

Figure 17:
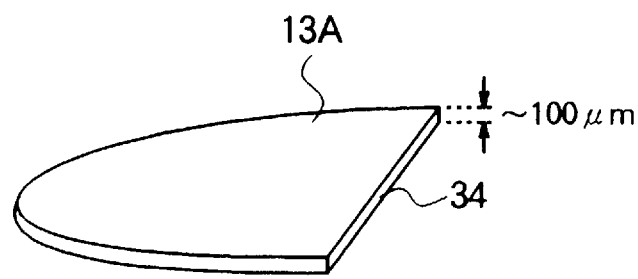
FIG. 17 illustrates the sample in FIG. 16 after lapping of the lower surface.
Figure 18:
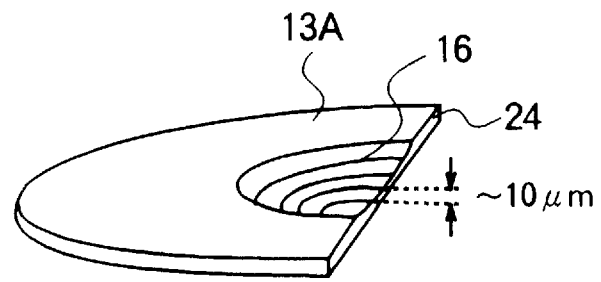
FIG. 18 illustrates the sample in FIG. 16 after dimpling of the lower surface.
Figure 19:
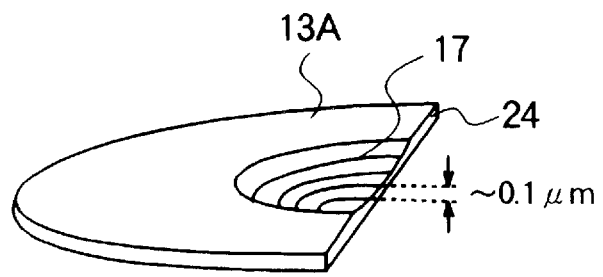
FIG. 19 illustrates the sample in FIG. 16 after ion milling of the dimple.

The underside 13A of the sample is then processed as described above. FIG. 17 shows the result of lapping the underside 13A. FIG. 18 shows the result of dimpling. FIG. 19 shows the result of ion milling. In the dimpling process, the center of the dimple 16 is aligned with respect to the cut edge 24, so that the fault site lies in the deepest part of the dimple, as shown in FIG. 18. The ion milling process illustrated in FIG. 19 can then be carried out so as to leave an accurately known thickness of substrate material below the fault site.

Figure 20:
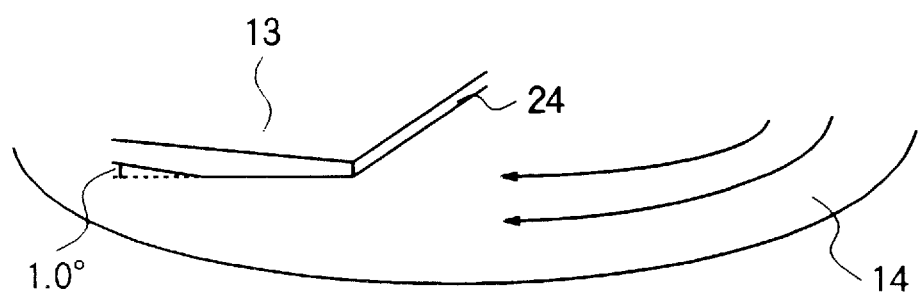
FIG. 20 illustrates a lapping process that can be employed instead of the dimpling shown in FIG. 18.

The third variation provides an alternative to the dimpling process. After the upper surface of the sample 13 has been lapped as in FIGS. 4 to 6, or as in the first variation in FIGS. 11 to 15, the sample is cut as illustrated in FIG. 16, and the underside 13A is lapped as illustrated in FIG. 17, reducing the sample thickness to substantially 100 μm, for example, as before. The sample 13 is then tilted at an angle of 1.0°, for example, as shown in FIG. 20, and is further lapped until a mirror finish is achieved and the cut edge 24 has been reduced to a knife-edge 25, as illustrated in FIG. 21.

Figure 21:
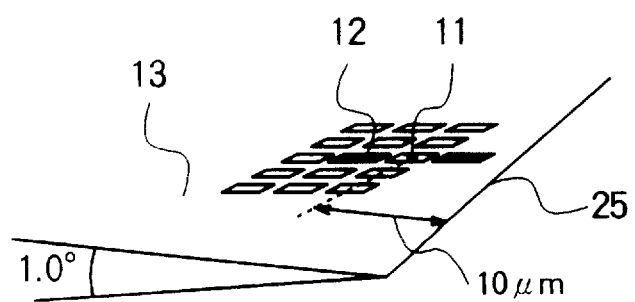
FIG. 21 illustrates the result of the lapping process in FIG. 20.

In FIG. 21, the thickness of the substrate at the fault site 11 is substantially 0.2 μm, as calculated by trigonometry from the angle 1.0° and distance 10 μm. This is sufficiently thin to permit TEM observation, but if necessary, the thickness can be further reduced by ion milling. Only a short milling time will be necessary. The thickness can also be reduced by reducing the above-mentioned angle from 1.0° to a smaller angle, or by reducing the above-mentioned distance from 10 μm to a smaller distance.

The invented method and variations described above all produce a plan-view sample that has no remaining parts that might obstruct TEM observations. The sample can be tilted freely inside the TEM. The electron beam is moreover able to penetrate the sample both at the fault site 11 and in a considerable surrounding area, where the sample has been thinned by ion milling as in FIGS. 9 and 19, or by lapping as in FIGS. 20 and 21. The defect that caused the fault can thus be adequately visualized. The first, second, and third variations enable the thickness of the substrate 21 or upper layers 22, or of both, to be calculated accurately, enabling the defect to be accurately characterized by techniques such as elemental analysis.

Next a few methods of using the samples described above to observe and take measurements of a fault in a semiconductor integrated circuit will be described. The basic theory of transmission electron microscopy is well known, so only a few points will be mentioned here.

The electron beam is accelerated by a high voltage, such as two hundred thousand volts (200 kV). For samples about 0.1 μm thick, this voltage produces a sharp TEM image. In a crystalline substance, electrons are diffracted according to the Bragg condition given by the equation $$n\lambda = 2d\sin\theta$$

where n is the order of reflection, λ is the wavelength of the electron beam, d is the spacing between crystal lattice planes, and θ is the angle between the electron beam and lattice planes. High-order diffracted electrons can be blocked by an appropriate objective aperture stop to obtain a high-contrast image. When a non-crystalline substance is observed, scattering rather than diffraction occurs, but the contrast can be similarly controlled by blocking electrons with large scattering angles.

Figure 22:
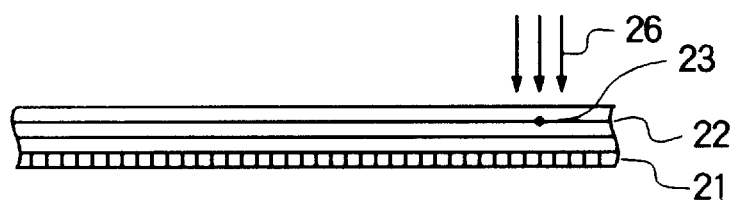
FIG. 22 illustrates TEM observation of a sample prepared as in FIGS. 1 to 9.

FIG. 22 illustrates the TEM observation of a sample prepared for analysis of a fault in one of the upper layers 22. The fault is due to a defect 23. The sample is prepared by the basic method illustrated in FIGS. 1 to 9, leaving the layer in which the fault occurred intact, but leaving only a small thickness of substrate 21. When the electron beam 26 passes through the sample, electrons are scattered by interaction with the atoms of the substrate 21 and upper layers 22, including atoms of the defect 23. The defect 23 can be detected and studied by taking measurements of the scattered electrons and analyzing the scattering. Due to the invented sample preparation method, the entire defect 23 and its surrounding region can be visualized and measured easily.

Figure 23:
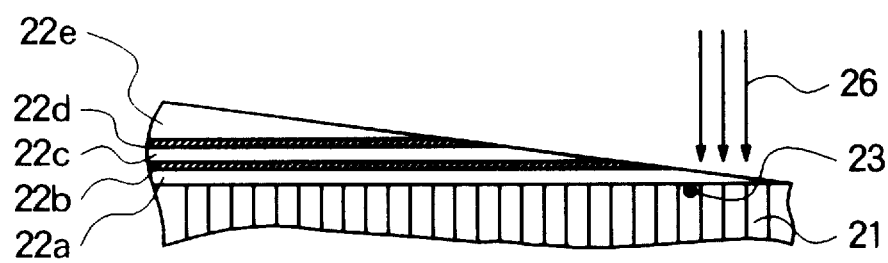
FIG. 23 illustrates TEM observation of a sample prepared as in FIGS. 11 to 15.

In FIG. 23, the fault is due to a defect 23 in the semiconductor substrate 21. The sample is prepared by the first variation of the invented method, removing most of the upper layers 22b to 22e above the fault site and leaving only a known thickness of the first insulating layer 22a. Since more of the upper layers are removed than in FIG. 22, more of the substrate 21 can be left.

The defect 23 is again studied by measuring the way in which the electron beam 26 is scattered. In particular, the technique of elemental analysis is applied, using the well-known thin-film approximation. The basic assumption of this approximation is that atoms of an element, such as a dopant element diffused into the substrate 21, are distributed uniformly throughout the sample. Before the measurements can be analyzed by this approximation, the effects of the remaining upper layers 22, which do not contain the element in question, must be subtracted. This can be done accurately, because with the first variation of the invented sample preparation method, the thickness of the upper layers 22 above the defect 23 is accurately known.

Figure 24:
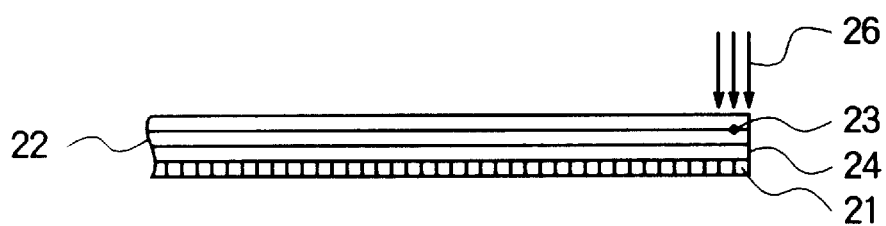
FIG. 24 illustrates TEM observation of a sample prepared as in FIGS. 16 to 19.
Figure 25:
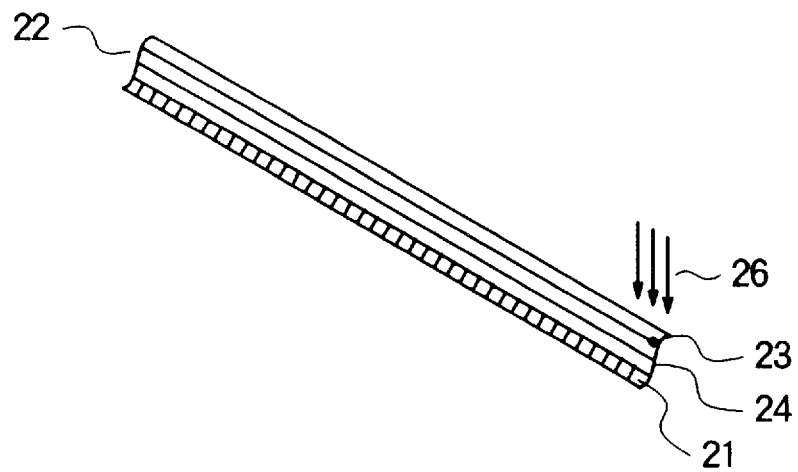
FIG. 25 illustrates the tilting of the sample in FIG. 24.

FIGS. 24 and 25 illustrate the analysis of another defect 23 in one of the upper layers 22. This time the sample has been prepared according to the second variation of the invented method, so the defect 23 is located close to the cut edge 24 of the sample. During the TEM observation the sample is tilted, permitting the electron beam 26 to pass through the defect 23 at a variety of angles. This enables various useful and well-known methods of analysis to be applied, such as the two-beam method and the stereo projection method. In addition, the thickness of the substrate 21 below the defect 23 is accurately known, because of accurate positioning of the dimple 16 in FIG. 18, so substrate effects can be accurately subtracted in the analysis.

Figure 26:
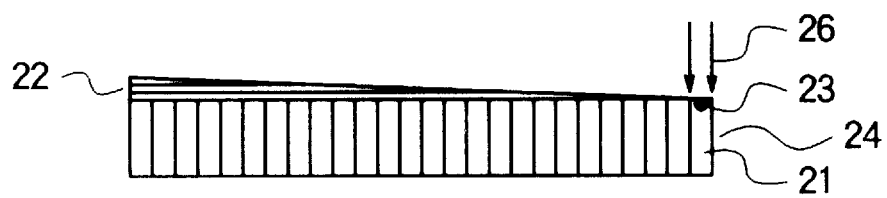
FIG. 26 illustrates TEM observation of a sample prepared as in FIGS. 11 to 19.
Figure 27:
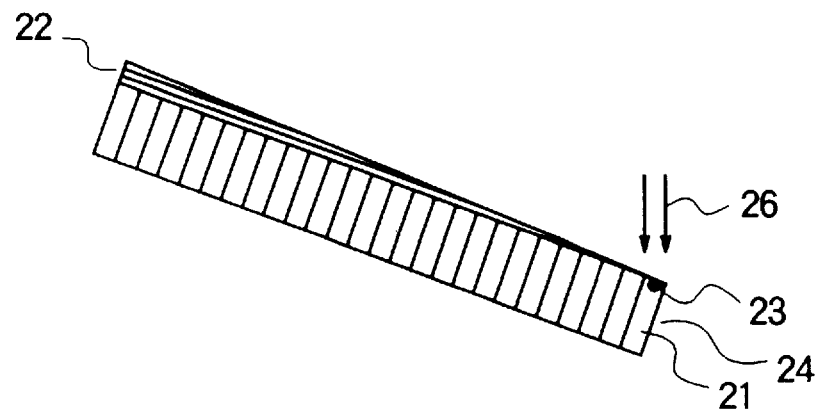
FIG. 27 illustrates the tilting of the sample in FIG. 26.

FIGS. 26 and 27 illustrate the similar analysis of a defect 23 located in the substrate 21. The sample has been prepared according to both the first and the second variations of the invented method, placing the defect 23 close to the cut edge 24 of the sample, under a known thickness of upper layers 22. Accurate analysis is possible by subtracting the small and known contribution of the remaining upper layers 22.

Figure 28:
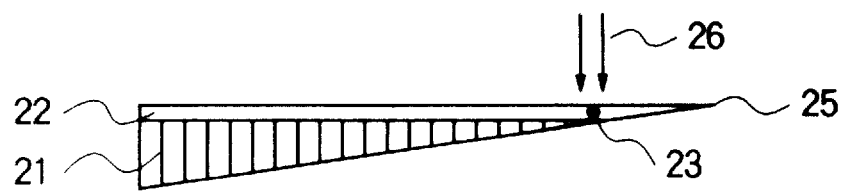
FIG. 28 illustrates TEM observation of a sample prepared as in FIGS. 20 and 21.
Figure 29:
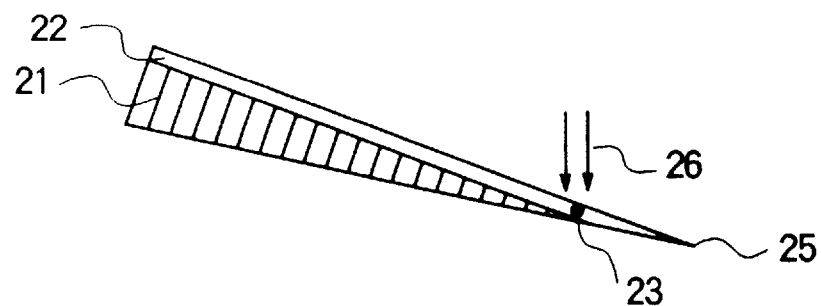
FIG. 29 illustrates the tilting of the sample in FIG. 28.

FIGS. 28 and 29 illustrate the analysis of a defect 23 located in the upper layers 22 of a sample prepared according to the third variation of the invention. This time it is the small and known contribution of the remaining substrate layer 21 that can be accurately subtracted.

Figure 30:
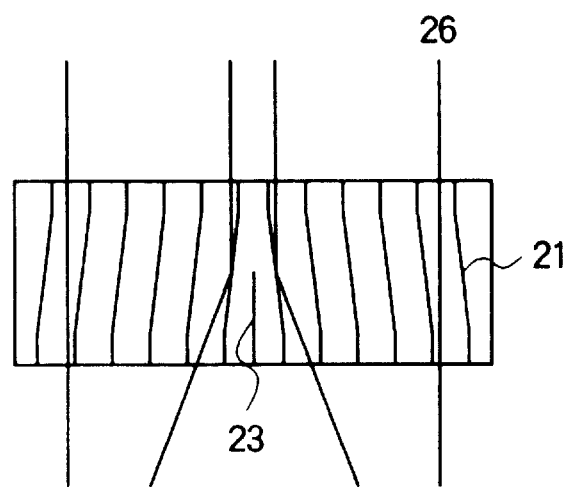
FIG. 30 illustrates scattering of an electron beam around a crystal dislocation.

FIG. 30 shows in more detail the scattering of electrons by a defect 23. The defect 23 is a dislocation in the crystal structure of the substrate 21. The dislocation causes strain in the surrounding crystal lattice, which perturbs the Bragg condition on scattered electrons around the edges of the dislocation, creating a contrast pattern in the TEM image. The TEM image accordingly does not reveal the central core of the defect 23, but rather the distortion in the surrounding lattice. The same is true when the defect 23 is caused by a set of lattice vacancies, or by precipitation, instead of by dislocation.

The general method of analyzing a dislocation fault starts by defining the dislocation in terms of its Burgers vector. This requires the sample to be tilted at a certain angle with respect to the electron beam 26, such that strong excitement is obtained for a particular diffracted electron, in addition to the transmitted electron (this is what is referred to as the two-beam condition). Mathematically, if g represents the vector of the excited diffraction electron, and if b is the Burgers vector, the contrast disappears when the sample is tilted at an angle such that following vector dot-product condition is satisfied:

$$g \cdot b = 0$$

The Burgers vector can therefore be determined by tilting the sample to find the angles that eliminate contrast. The necessary tilt angles are large, but with the invented sample preparation methods, tilting the sample at a large angle presents no particular problem.

It is also possible to eliminate the contrast due to the lattice distortion and observe the core of the defect 23 directly, using a the so-called the weak-beam condition, which is a further application of the two-beam condition.

Next, the invented methods of sample preparation and TEM observation will be compared with a conventional method of preparing and observing a cross-sectional sample of a faulty integrated circuit.

Figure 31:
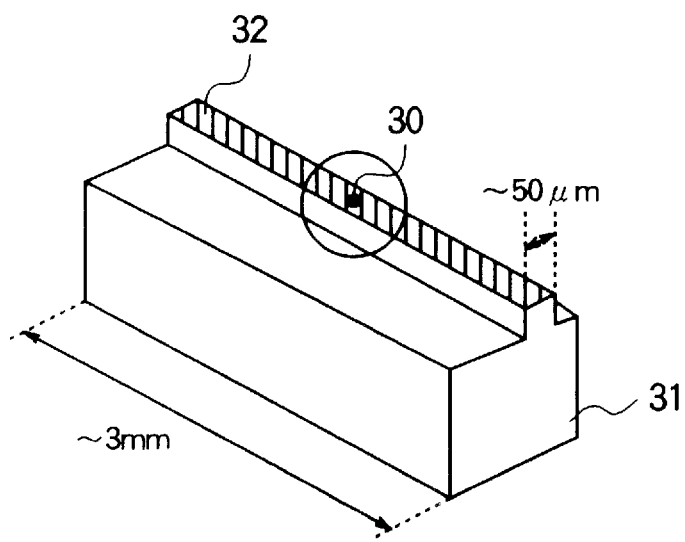
FIG. 31 illustrates the first steps in a conventional sample preparation method.

Referring to FIG. 31, in the conventional method, the fault site 30 is located and a sample 31 having the general shape of a rectangular prism about three millimeters long is cut from the integrated circuit with a dicing saw. Ion milling is then used to isolate a strip 32 about fifty micrometers wide, containing the fault site 30, on the upper surface of the sample 31.

Figure 32:
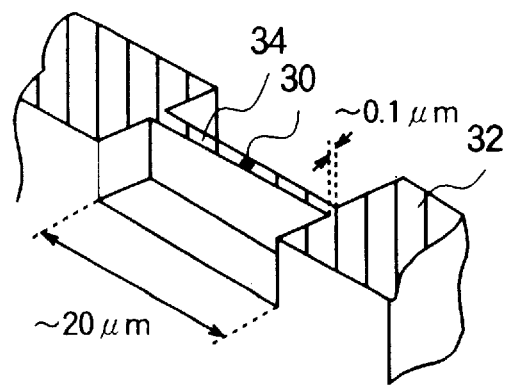
FIG. 32 illustrates a further step in this conventional method.

Referring to FIG. 32, in a region about twenty micrometers long in the vicinity of the fault site 30, the strip 32 is thinned by focused ion-beam (FIB) processing to leave a slice 34 about 0.1 µm thick. When placed in the TEM, the sample is turned on its side as shown in FIG. 33, so that the electron beam 26 can penetrate the thin slice 34.

Figure 33:
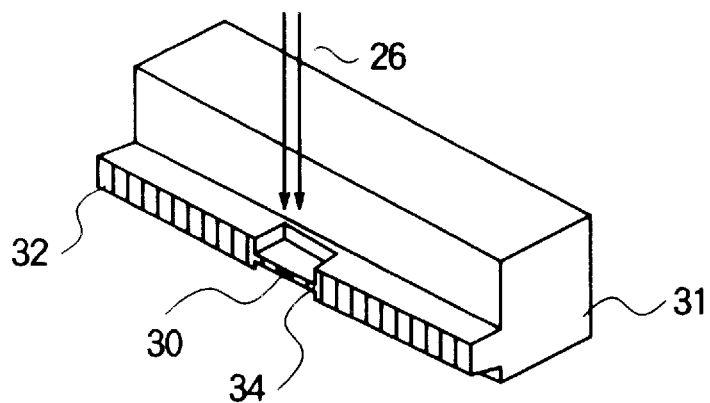
FIG. 33 illustrates TEM observation of a sample prepared as in FIGS. 31 and 32.

As is evident from FIG. 33, the remaining bulk of the sample 31 restricts the angles at which the sample can be tilted in the TEM. Moreover, the size of the area that can be thinned is restricted because the thinned slice 34 is supported on only three sides.

Compared with this conventional method, the invented sample preparation method enables a larger area to be observed at more angles. More information can accordingly be obtained. When an integrated-circuit fault is caused by a crystal defect, a plan-view sample prepared by the invented method consistently enables the entire defect and its surrounding area to be visualized, measured, and analyzed by transmission electron microscopy. This is in major contrast to the conventional method illustrated in FIGS. 31 to 33, in which it is difficult to ensure that the thin slice 34 will intersect the defect at all, let alone provide complete visualization.

While the invented method is particularly useful in the analysis of faulty VLSI and ULSI devices, the invention can be practiced with any type of integrated circuit. It is not necessary for the sample to be round. If the upper surface of the sample is lapped while the sample is held in a fixed position, as in FIGS. 11 to 15, for example, the sample can have any convenient shape, and can be excised by various methods, not limited to the use of a dicing saw.

Those skilled in the art will recognize that further variations are possible within the scope claimed below.

What is claimed is:

1. A method of preparing a plan-view sample of a faulty element for observation with a transmission electron microscope, comprising:

marking a faulty portion of said element;

excising from said element a sample small enough to be held in said transmission electron microscope, said sample having an upper surface near which said faulty portion is located, and a lower surface opposite to said upper surface;

lapping both said upper surface and said lower surface; and further thinning the lower surface of said sample, in a region below said faulty portion, to a thickness permitting an electron beam in said transmission electron microscope to penetrate through said samples;

wherein said element is an integrated circuit, and said faulty portion is a circuit element of said integrated circuit, and wherein said lapping both said upper surface and said lower surface includes reducing all parts of said sample to a thickness of less than two hundred micrometers.

2. The method of claim 1, wherein, in said lapping both said upper surface and said lower surface, said upper surface is lapped to a mirror finish.

3. The method of claim 1, wherein said further thinning the lower surface of said sample comprises forming a dimple in said lower surface; and ion-milling said lower surface within said dimple.

4. The method of claim 1, wherein said element comprises a substrate and a plurality of upper layers overlying said substrate, and wherein, in said lapping both said upper surface and said lower surface, said upper surface is lapped until a boundary of an exposed area of said substrate approaches a predetermined distance from said faulty portion.

5. The method of claim 4, wherein said sample is rotated during said lapping both said upper surface and said lower surface, so that said substrate becomes exposed on all sides of said faulty.

6. The method of claim 4, wherein said sample is held at a predetermined angle while said upper surface is being lapped in said lapping both said upper surface and said lower surface, so that when the boundary of said exposed area of said substrate approaches said predetermined distance from said faulty portion, a known thickness of said upper layers is left above said faulty portion.

7. The method of claim 1, further comprising:

cutting said sample along a line disposed a certain distance from said faulty portion, thereby creating a cut edge at a known distance from said faulty portion.

8. The method of claim 7, wherein said further thinning the lower surface of said sample comprises:

forming a dimple in a certain positional relationship to said cut edge, so that said dimple is centered beneath said faulty portion.

9. The method of claim 8, wherein said further thinning the lower surface of said sample also comprises ion milling of said lower surface within said dimple.

10. The method of claim 7, wherein said further thinning the lower surface of said sample comprises:

holding said sample at a certain angle and lapping said lower surface until said cut edge becomes a knife edge, thereby leaving a known thickness of said substrate below said faulty portion.

11. A method of measuring a defect in an element having a substrate covered by upper layers, said defect being disposed in said substrate, comprising:

preparing a plan-view sample from said element, said plan-view sample having a known thickness of said upper layers above said defect;

placing said plan-view sample in a transmission electron microscope;

taking measurements of scattering of an electron beam by said plan-view sample in said transmission electron microscope, in a vicinity of said defect; and subtracting effects of said known thickness of said upper layers from said measurements;

wherein said preparing a plan-view sample comprises marking a faulty portion of said element; excising from said element a sample small enough to be held in said transmission electron microscope, said sample having an upper surface near which said faulty portion is located, and a lower surface opposite to said upper surface; lapping both said upper surface and said lower surface; and further thinning the lower surface of said sample, in a region below said faulty portion, to a thickness permitting an electron beam in said transmission electron microscope to penetrate through said sample;

wherein said element is an integrated circuit, and said faulty portion is a circuit element of said integrated circuit, and wherein said lapping both said upper surface and said lower surface includes reducing all parts of said sample to a thickness of less than two hundred micrometers.

12. The method of claim 11, wherein said taking measurements employs elemental analysis.

13. The method of claim 11, further comprising tilting said plan-view sample at various angles in said transmission electron microscope.

14. The method of claim 13, wherein said taking measurements employs a two-beam method.

15. The method of claim 11, wherein said preparing a plan-view sample further comprises:

holding said sample at a predetermined angle against a lap; and lapping an upper surface of said sample to a mirror finish, until said substrate is exposed to within a certain distance from said defect.

16. A method of measuring a defect in an element having a substrate covered by upper layers, said defect being disposed in said upper layers, comprising:

preparing a plan-view sample from said element, said plan-view sample having a known thickness of said substrate below said defect;

placing said plan-view sample in a transmission electron microscope;

taking measurements of scattering of an electron beam by said plan-view sample in said transmission electron microscope, in a vicinity of said defect; and subtracting effects of said known thickness of said substrate from said measurements;

wherein said preparing a plan-view sample comprises marking a faulty portion of said element; excising from said element a sample small enough to be held in said transmission electron microscope, said sample having an upper surface near which said faulty portion is located, and a lower surface opposite to said upper surface; lapping both said upper surface and said lower surface; and further thinning the lower surface of said sample, in a region below said faulty portion, to a thickness permitting an electron beam in said transmission electron microscope to penetrate through said sample;

wherein said element is an integrated circuit, and said faulty portion is a circuit element of said integrated circuit, and wherein said lapping both said upper surface and said lower surface includes reducing all parts of said sample to a thickness of less than two hundred micrometers.

17. The method of claim 16, wherein said taking measurements employs elemental analysis.

18. The method of claim 16, further comprising tilting said sample at various angles in said transmission electron microscope.

19. The method of claim 18, wherein said taking measurements employs a two-beam method.

20. The method of claim 16, wherein said preparing a plan-view sample further comprises:

cutting said sample at a predetermined distance from said defect, thereby producing a cut edge;

holding said sample at a predetermined angle against a lap; and lapping a lower surface of said sample to a mirror finish, until said cut edge is reduced to a knife edge.

* * * * *